United States Patent [19]

Inokuchi et al.

[11] Patent Number: 4,676,258

[45] Date of Patent: Jun. 30, 1987

[54] DEVICE FOR HYPERTHERMIA

[75] Inventors: Kiyoshi Inokuchi; Keizo Sugimachi, both of Fukuoka; Toshiharu Shirakami, Hino; Hidenobu Kai, Fukuoka; Yoshio Kawai, Musashino; Tetsuya Hotta, Hoya, all of Japan

[73] Assignee: Kureha Kagaku Kogyo Kabushiki Kaisha, Tokyo, Japan

[21] Appl. No.: 873,095

[22] Filed: Jun. 5, 1986

Related U.S. Application Data

[63] Continuation of Ser. No. 572,253, Jan. 20, 1984, abandoned.

[30] Foreign Application Priority Data

Jan. 24, 1983 [JP] Japan .................................. 58-9658
Jun. 6, 1983 [JP] Japan .............................. 58-100616
Dec. 1, 1983 [JP] Japan .............................. 58-227144

[51] Int. Cl.⁴ ............................................ A61N 5/00
[52] U.S. Cl. .................................... 128/804; 128/401
[58] Field of Search ..................... 128/804, 399–402, 128/784–786

[56] References Cited

U.S. PATENT DOCUMENTS 3,125,096 3/1964 Antiles et al. ...................... 128/401
4,016,886 4/1977 Doss et al. .......................... 128/804
4,140,130 2/1979 Storm, III .......................... 128/804
4,375,220 3/1983 Matvias .............................. 128/804

FOREIGN PATENT DOCUMENTS 2407559 8/1975 Fed. Rep. of Germany ...... 128/804
WO81/03616 12/1981 PCT Int'l Appl. .................. 128/804

Primary Examiner—Lee S. Cohen
Attorney, Agent, or Firm—Oblon, Fisher, Spivak, McClelland & Maier

[57] ABSTRACT

A device for radio-frequency hyperthermia having a first electrode adapted to be disposed in a tract organ of a living body.

A second electrode is provided which is adapted to be disposed on an outer circumference of the living body such that the second electrode is opposed to the first electrode such that there is generated a spatially inhomogeneous electric field within the living body in cooperation with the first electrode so that a part of the living body near the first electrode may be heated more strongly than a part of the living body near the second electrode.

This serves to selectively heat a tumor or malignancy region at the deep inside of the living body by a noninvasive technique.

29 Claims, 25 Drawing Figures

Fig. 6
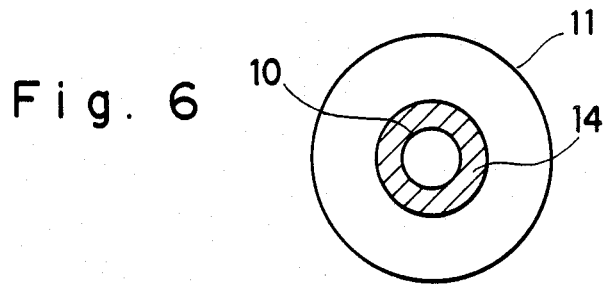
Fig. 7
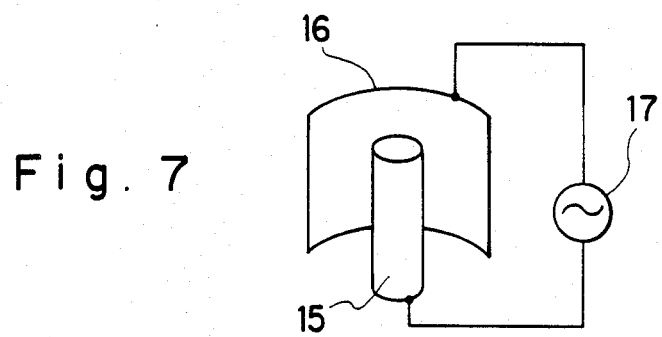
Fig. 8

DEVICE FOR HYPERTHERMIA

This application is a continuation of application Ser. No. 572,253, filed Jan. 20, 1984, now abandoned.

BACKGROUND OF THE INVENTION

This invention concerns a device for hyperthermia and, more specifically, it relates to a high-frequency heating electrodes device, in particular, a high-frequency electrodes device for medical use which can be applied to the hyperthermia therapy of tumors or cancers.

This invention further relates to an improvement of at least one of paired electrodes for use in the high-frequency device for hyperthermia.

High-frequency hyperthermia therapy has been known in which the high-frequency energy, typically radio-frequency energy, is applied to a lesion portion of a patient in the form of heat for therapy where the nature of the cancer that the cancer cells are less resistant to heat or elevated temperature than normal cells is utilized.

The hyperthermia therapy has been carried out in the conventional high-frequency heating technique, for instance as shown in FIGS. 1 and 2, by disposing a pair of plate-like electrodes 4, 5 on opposed surface positions of a living body 1 so that a region 3 including a part 2 to be heated of the living body 1 may be situated between the two plate-like electrodes 4 and 5, and by supplying a high-frequency current from a high-frequency power supply 6 through the electrodes, 4, 5 disposed on the sides of the belly and the back.

However, the high-frequency currents pass substantially in parallel throughout the region 3 between the opposing electrodes 4, 5 according to this conventional technique, which results in the undesirable heating of portions other than the part or portion 2 intended to be heated. Moreover, there is fear that a subcutaneous fat layer 7 may be heated more strongly than the intended portion 2 due to the differences in the electric properties or factors such as the electric conductivity and the dielectric constant between the subcutaneous fat layer 7 and the tissue of the tract organ including the lesion part 2. It has thus been difficult to heat or warm the lesion part 2 at the deep inside of the living body to a temperature desired for the hyperthermia therapy because of the patient's complaint about heat and the risk of scalding of the epidermis tissue.

As one of the techniques for overcoming the foregoing problems, it has been attempted to dispose a pointed electrically conductive member such as a metallic needle at the aimed or intended part to be heated for locally applying the heat thereto by concentrating the electric field between the opposed plate-like electrodes on the aimed part around the metallic needle. Although this technique is effective for concentrating the electric field on the aimed part, it is not always preferred because surgical skills are required for inserting and extracting the metallic needle or the like, and because much pain is given to the patient for the technique is essentially invasive.

SUMMARY OF THE INVENTION

This invention has been made in view of the foregoings and the object thereof is to provide a device for hyperthermia capable of selectively heating or warming a predetermined region at the deep inside of a living body by a noninvasive technique without giving much pain to a patient.

The above object can be attained in accordance with this invention by a device for hyperthermia comprising first electrode adapted to be disposed in a tract organ of a living body and a second electrode adapted to be disposed on an outer circumference of the living body such that the second electrode is opposed to the first electrode so as to generate a spatially inhomogeneous electric field within the living body in cooperation with the first electrode so that a part of the living body near the first electrode may be heated more strongly than a part of the living body near the second electrode.

In one preferred embodiment of the device for hyperthermia according to this invention, the first electrode adapted to be disposed in the tract organ is formed entirely in the form of a hollow cylinder or tube, and the second electrode adapted to be disposed on the outer circumference of the living body is formed entirely in the form of a curved or flat plate of a relatively large area, in which a high-frequency current, typically radio-frequency current of about 3–30 MHz is supplied at a power, for example, of about 10–300 W through the two electrodes to establish an inhomogeneous electric field which is stronger at a region near the first electrode than at a region near the second electrode and enables the selective heating of the lesion portion at the deep inside of the living body near the first electrode.

Further, since the first electrode is designed to be disposed in the tract organ, the first electrode can be easily disposed or inserted and extracted through mouth, anus, vagina or the like, while minimizing the pains given to the patient.

In addition, according to this invention, the first electrode of the device for hyperthermia adapted to be situated in the tract organ of the living body, that is, an endotract electrode comprising an electrode element for producing the spatially inhomogeneous high-frequency electric field, a bag-like member made of a thin polymeric film for surrounding the electrode element, and means for introducing and discharging a cooling liquid into and out of an inside of the bag-like member is provided so as to attain the above-mentioned object.

Further object of this invention is to provide the first or endotract electrode which has little risk of giving an exessive pressure to a wall of the tract organ.

According to this, invention, the further object can be attained by the first or endotract electrode wherein the bag-like member comprises a flexible bag-like member having sizes large enough to be contacted with an inner surface of the tract organ without being expanded.

Still further object of this invention is to provide the first or endotract electrode which enables to heat or warm the region at the deep inside of the living body at a desired temperature.

According to this invention, the still further object can be attained by the first or endotract electrode wherein the first electrode further comprises means for detecting a temperature fixed on an outer surface of the flexible bag-like member having sizes large enough to be contacted with an inner surface of the tract organ without being expanded.

DESCRIPTION OF THE ACCOMPANYING DRAWINGS

Hereinafter, the invention will be described in more detail by referring to the accompanying drawings, by which the foregoing and other objects, as well as the features of this invention will be made clearer, in which:

FIG. 1 and FIG. 2 are schematic explanatory views of a conventional medical heating device, FIG. 2 corresponding to a cross section along line II—II in FIG. 1, FIG. 3 is a schematic explanatory view of a preferred embodiment of a device for hyperthermia according to this invention, FIG. 4 is an explantory graph showing a spatial distribution of the electric field produced by the device shown in FIG. 3, FIG. 5 is an explanatory graph showing a spatial distribution of the consumption of the high-frequency energy or power given by the device shown in FIG. 3, FIG. 6 is an explanatory view for illustrating the mode of heating by the device shown in FIG. 3, FIG. 7 is a schematic explanatory view of another preferred embodiment of a device for hyperthermia according to this invention, FIG. 8 is an explanatory view for illustrating the mode of heating by the device shown in FIG. 7, FIGS. 9 is a schematic explanatory view showing an application of the device of FIG. 7, FIG. 10 is an explanatory sectional view along line X—X in FIG. 9, FIG. 11 is an explanatory sectional view showing the detail of a first or endotract electrode of one preferred embodiment according to this invention, FIG. 12 is an explanatory view showing the detail of a first or endotract electrode of another preferred embodiment according to this invention, FIG. 13 is an explanatory sectional view of the electrode along a line XIII—XIII in FIG. 12, FIG. 14 is an explanatory enlarged view of a portion XIV in FIG. 12, FIG. 15 is an explanatory sectional view of the electrode along a line XV—XV in FIG. 12, FIG. 16 is an explanatory sectional view of the electrode along a line XVI—XVI in FIG. 12, FIG. 17 is an explanatory sectional view, similar to FIG. 16, of the electrode in which a bag-like member is in a folded state, FIG. 18 is an explanatory view of a connector for thermocouples of the electrode of FIG. 12, FIG. 19 and FIG. 20 are explanatory views of one example of a second electrode structure, FIGS. 21 through 23 are explanatory views of an example where heat is applied to the dog's esophagus by using the electrodes shown in FIGS. 11 and 19, in which FIG. 21 is an explanatory sectional view showing an arrangement of the paired electrodes, FIG. 22 is an enlarged sectional view showing a region near the esophagus shown in FIG. 21, and FIG. 23 is a graph showing the changes in the temperatures at various parts during heating with respect to time, and FIGS. 24 and 25 are graphs showing the changes in the temperatures with respect to time during heating by using the endotract electrode of FIG. 12 and the electrode for comparison respectively.

DESCRIPTION OF PREFERRED EMBODIMENT

Figure 1:
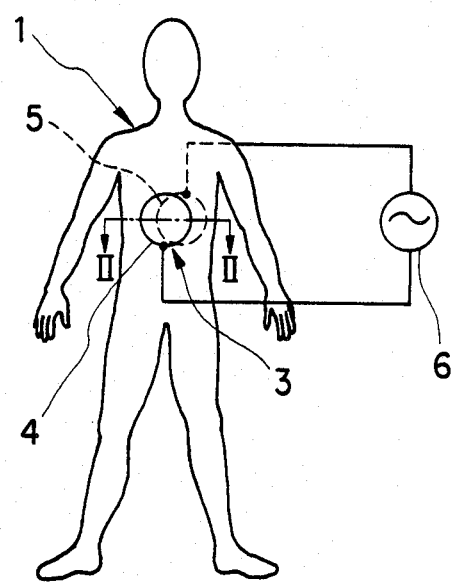
Figure 2:
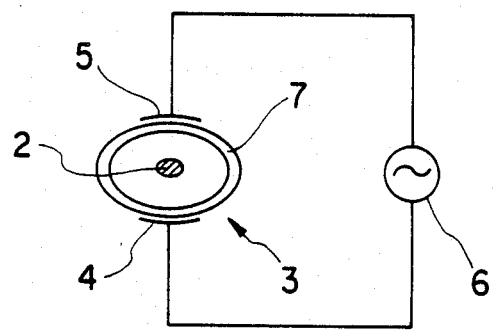
Figure 3:
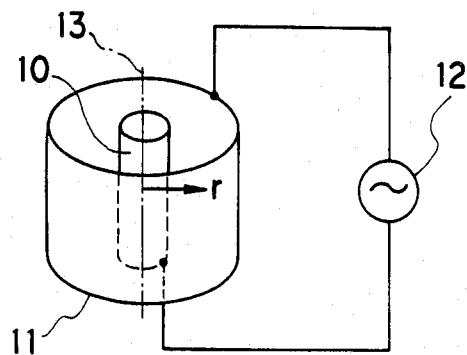
Figure 4:
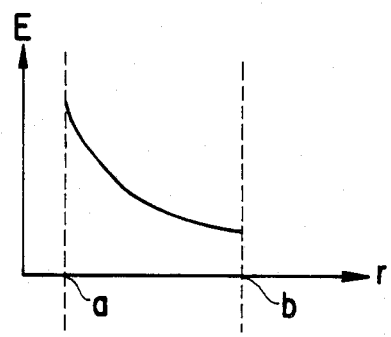
Figure 5:
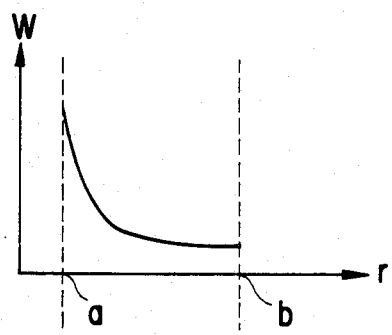

The device for hyperthermia according to this invention using an endotract first electrode of this invention will be outlined referring to FIGS. 3 through 8. In FIG. 3, coaxially disposed cylindrical first electrode 10 (radius:a) and a hollow cylindrical second electrode 11 (radius:b>a) are connected respectively to a high-frequency power supply 12. It is assumed here for the sake of simplicity of explanation that the space between the two electrodes 10 and 11 is uniformly filled with an isotropic medium having constant electric properties in view of an electric conductivity and a dielectric constant. Neglecting the distortion of the electric field near the upper and lower ends of the electrodes 10 and 11, the lines of electric force are expanded radially in the region between the two electrodes 10, 11 and the electric field intensity E is decreased in an inverse proportion to the distance r from a central axis 13 in the form of $E \propto 1/r$ as shown in FIG. 4. Since the amount of heat generation W per unit volume is represented by (electric conductivity)×(electric field intensity)$^2$ for a unit period of time, the amount of heat generation or power consumption W changes in an inverse proportion to $r^2$ in the form of $W \propto 1/r^2$ as shown in FIG. 5, whereby a region 14 near the first electrode 10 is strongly or intensely heated much more than the other region as shown in FIG. 6.

While on the other hand, in a case where a cylindrical first electrode 15 and a second electrode 16 in the shape of an arcuate or curved plate formed by a portion of the hollow cylindrical electrode 11 are connected to a high-frequency power supply 17 as shown in FIG. 7, the distribution of the electric field can not be expressed in such a simple manner as in FIG. 4, but it will be qualitatively true that the region of the relative strong electric field or the selectively heated region is situated near the first electrode 15 while deviated or shifted toward the second electrode 16 as shown by a reference numeral 18 in FIG. 8. The second electrode 16 may be replaced by a flexible plate-like member such as a flexible plate or a mesh in the form of a plate.

In the actual heating or warming of the living body, although the distribution of the electric field is complicated due to the unevenness or variation in the electric properties, i.e. electric conductivity and dielectric constant, depending on parts of the living body, it is true that a certain region near the first electrode is heated much stronger than the other regions.

What is required for the first electrode adapted to be disposed in the tract of the living body is that the first electrode, more specifically metallic portion of the first electrode, should be thin enough to be disposed or inserted in the tract organ and has an outer surface entirely of a large curvature so that the intensity or magnitude of the electric field near the first electrode is greater than that near the second electrode. The first electrode may have a shape of elliptic tube, square tube or the like instead of the circular tube or hollow cylinder. The first electrode may be composed of multiple small conductors such as conductor segments or conductive wires connected electrically to each other. Although it is preferred that the first electrode is constituted in the form of a hollow structure so as to define a passage for cooling medium therein as described later, it may be of a solid structure.

The second electrode may also be composed of multiple conductive members connected electrically to each other instead of a sheet of curved or flat conductor plate, so long as an area of the second electrode is entirely or generally formed larger than that of the first electrode, so that the electric field near and at a part of the second electrode in contact with the living body is relatively weaker than that near the first electrode.

Figure 9:
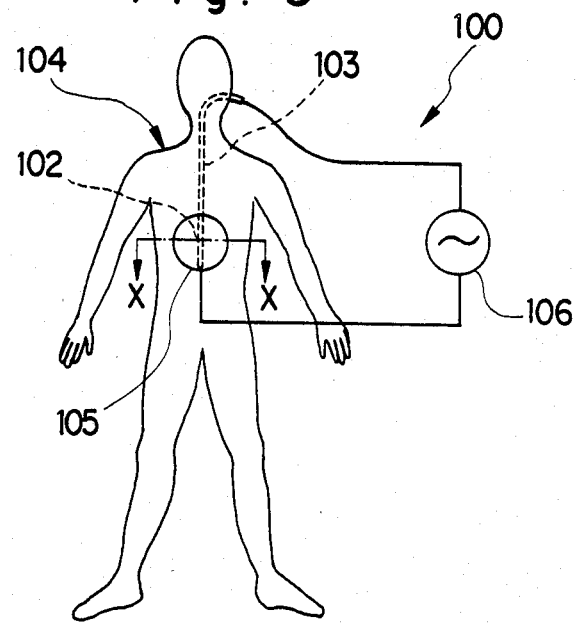
Figure 10:
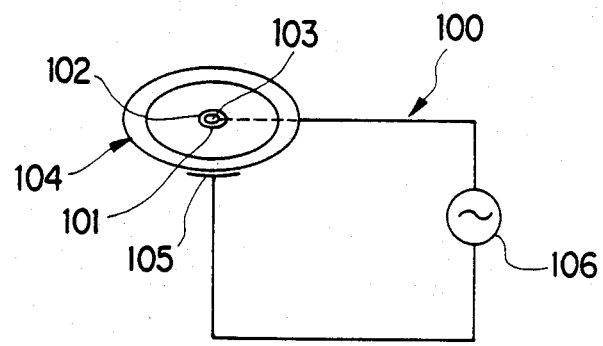

FIGS. 9 and 10 illustrate an example of an application of the device for hyperthermia 100 similar to the device shown in FIGS. 7 and 8 to therapy of the tumors 101 in the esophagus 102.

In FIGS. 9 and 10, the high-frequency heating device 5 comprises a first or endotract electrode 103 adapted to be disposed in the esophagus 102 of a living body 104, a second or outer electrode 105 having larger curvature as a whole than the endotract electrode 103 and adapted to be disposed on an outer circumference or surface of the living body 104 such that the outer electrode 105 is opposed to the endotract electrode 103 so as to position the lesion portion to be heated 101 therebetween, and a high-frequency power supply 106 of adjustable output frequency and power for example, adapted to pass a high-frequency current of the order of 3 to 30 MHz at the power of about 10 to 300 W through the paired electrodes 103, 105. The lesion portion to be heated 101 which is situated between the electrodes 103, 105 and near the endotract electrode 103 can be selectively heated by this device 100, because higher or stronger electric field will be produced in the vicinity of the endotract electrode 103 having larger curvature than the outer electrode 105.

One preferred embodiment of the first or endotract electrode according to this invention will now be described more in detail referring to FIG. 11.

Figure 11:
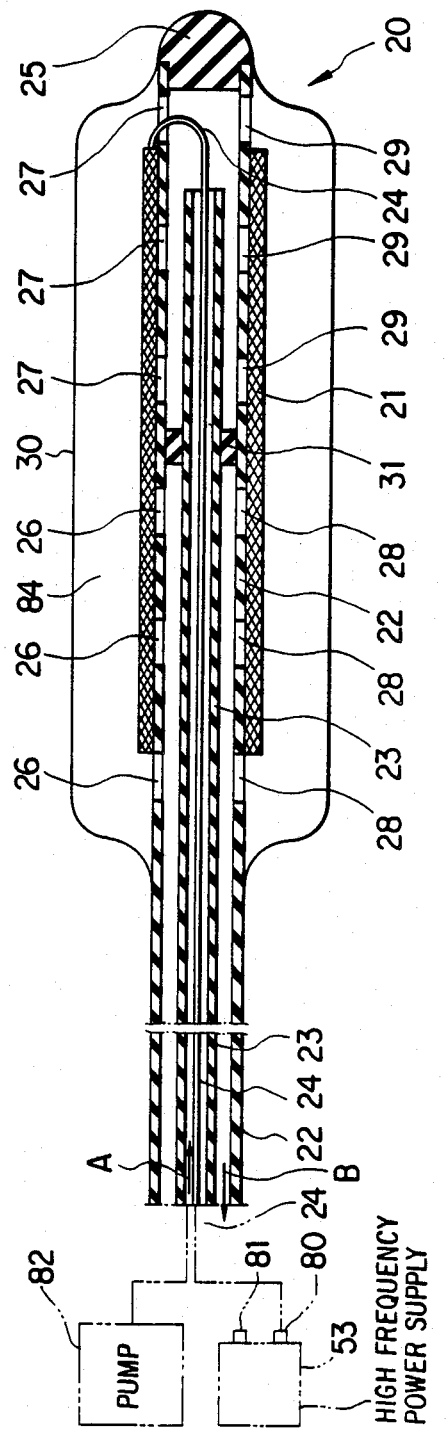

FIG. 11 shows a longitudinal cross section of an endotract electrode 20 as the first electrode including an electrode element 21. The hollow cylindrical first electrode element 21 is disposed or fixed on an outer cylindrical tube 22 as a support and connected by means of a lead wire 24 extended through an inner cylindrical tube 23 to one terminal 80 of the output terminals 80, 81 of a high-frequency power supply 53. Another terminal 81 is for the second electrode (not shown). The inner cylindrical tube 23 and the outer cylindrical tube 22 serve as a water introducing or charging pipe and a water discharging pipe as described later. It is desired that the electrode 20 is formed flexible so that it can be inserted into and extracted from a tract organ having a lesion portion to be subjected to hyperthermia therapy or heating treatment. Therefore, it is desired that the inner cylindrical tube 23 and the outer cylindrical tube 22 are made of polymeric material such as rubber, soft vinyl chloride or silicone and the electrode 21 is preferably composed of flexible component(s) such as metal foil(s) or braided metal wires made of copper or the like.

Reference will now be made to the water passing system in the endotract electrode 20 including the first electrode element 21 The outer cylindrical tube 22 is sealed at one end thereof by an end plug 25, and formed with a plurality of water passing apertures 26, 27, 28 and 29 at the circumferential wall thereof near the electrode element 21. A balloon-like member 30 as a bag-like member made of an expansible polymeric thin film is bonded at both ends thereof to the outer cylindrical tube 22 and to the end plug 25. When the endotract electrode 20 including the first electrode element 21 is disposed at the inside of a tract organ intended to be heated and water is fed or introduced through the inner cylindrical tube 23 in the direction A from a pump 82, the water flows from the apertures 27, 29 on the right-hand side of a sealing plug 31 made of silicone sealing material disposed between the inner and outer cylinders 22 and 23 through gaps in the braided wires electrode element 21 and/or through a gap between the electrode element 21 and the outer cylindrical tube 22 and then flows into a space 84 around the outer cylindrical tube 22, whereby the balloon-like member 30 begins to expand. When the feed of water is continued, the balloon-like member 30 expands till it contacts the inner wall or inner surface of the tract organ. The excess water flows from the apertures 26 and 28 on the left-hand side of the sealing plug 31 through gaps in the electrode element 21 and/or through the gap between the electrode element 21 and the outer cylindrical tube 22 into the outer cylindrical tube 22 and is then discharged by way of the outer cylindrical tube 22 in the direction B. Alternatively, the water may be fed through a tubular passage between tubes 22, 23 and discharged through a cylindrical passage in the tube 23. The flow rate of the circulated water may be controlled by the pump 82. The temperature of the water to be circulated may be controlled by cooling means (not shown).

The circulated liquid such as water provides two advantageous effects. Firstly, as a gap between the electrode element 21 and the inner wall of the tract organ can be filled with water for example, having electric factors (electric conductivity and dielectric constant) similar to those of the living body, the electric power loss which would not be negligible at the presence of the gap can be decreased to enable an effective high-frequency heating of the lesion at the wall of the tract organ. Secondly, since the electric field intensity is highest at the surface of the electrode element 21, there is fear that extremely excessive heat might be generated near the electrode element 21 to cause scalding at a portion of the inner wall of the tract organ if the water is not circulated. Such risk or fear of scalding can however be avoided by forcively cooling the very portion of the organ by means of the circulated water. The cooling liquid may be any electrically conductive liquid such as a saline water or other aqueous solutions provided that the liquid may give the foregoing two advantageous effects.

The outer diameter of the electrode structure 20 may be selected optionally so long as it is smaller than or equal to the inner diameter of the tract organ and the length of the electrode element 21 can also be selected optionally depending on the length of the lesion or part to be heated.

However, it should be noted that, when the expansible balloon-like member 30 has so small a natural or unexpanded diameter that the balloon-like member 30 is required to be expanded by giving pressure or by introducing pressurized liquid in the space 84 of the balloon-like member 30 so that the balloon-like member 30 may be closely contacted with the inner surface of the tract organ for the effective supply of the high-frequency current to the lesion portion, it is difficult to determine or control the pressure of the liquid to be given. If the given pressure is not sufficient the balloon-like member 30 will not get in close contact with the inner surface of the tract organ over the desired area. On the contrary, if the given pressure is much higher than desired, there is fear that the excessive pressure may be given to the tract organ when the balloon-like member is expanded under pressure. Thus, it will be difficult to maintain the pressure given from the balloon to the wall of the esophagus 102 within an allowable pressure limit (30 to 40 mmHg in general) in applying the endotract electrode 20 of FIG. 11 to the hyperthermia therapy of the tumors in the esophagus 102.

FIGS. 12 to 18 shows the details of another preferred embodiment of the first or endotract electrode 103a in which above-mentioned disadvantage of the electrode 20 is overcome or at least reduced.

In FIGS. 12 to 18, reference numeral 108 represents a flexible two-channel tube made of silicone rubber in which a passage or channel for introducing cooling liquid 109 and a passage or channel for discharging the cooling liquid 110, are integrally formed. The tube 108 is preferably made thin so that the tube 108 can be easily inserted into or extracted from a given tract organ so long as the tube 108 allows sufficient flow of the cooling liquid through the passages 109, 110 at a low passage resistances or at low pressure drops in the liquid flow. When the endotract electrode 103a is designed to be applied to the esophagus, the tube 108 having 5 to 6 mm in the outer diameter thereof and 70 to 80 cm in the length thereof for example, may be selected. The tube 108 may have more than or equal to three channels of liquid passages and may be made of an appropriate non-toxic, insulating and flexible material instead of the silicone rubber.

At a top end side of the tube 108 are attached a flexible electrode element 111 and a flexible bag-like member 112 having sizes large enough to be contacted with an inner surface of a tract organ without being expanded. While at another end side of the tube 108 are connectors 113 and 114 integrally connected with the introducing passage means 109 and the discharging passage means 110 respectively. The connecting portions of the connectors 113, 114 with the tube 108 are made hard by a adhesive of silicone resin or other appropriate adhesives and are further covered over by a heat-shrinkable tube 108a made of silicone.

The electrode element 111 comprises a braided metallic wires in the form of a tube fixed on the outer circumference of the tube 108. The electrode element 111 may alternatively comprise other conductive and flexible members such as bellows or helical element. The electrode element 111 is formed to have approximately the same axial length as that of the lesion or tumor portion. The metallic wire for the braid 111 is made of a material such as stainless steel or tin-plated copper.

A top end 116 of a lead wire 115, having 1 mm of diameter for example, for supplying the high-frequency energy is electrically connected and fixed to one end of the electrode element 111. The lead wire 115 is extended along the outer surface of the tube 108 up to a position near the connectors 113, 114, and at the extended end of the lead wire 115 is provided an electrical connector 117 to be connected to a high-frequency power supply 106a.

The bag-like member 112 is made generally in the form of a hollow cylinder for example, so as to be fitted with the sizes and shape of the tract organ around the lesion portion to be treated, or with the sizes and shape of a narrowed or throttled portion or arctation portion due to the tumor or cancer, and is fixed to the outer circumference of the tube 108 at both ends of a reduced diameter 118, 119 so as to surround the electrode element 111. The bag-like member 112 may be made in the other forms or shapes than the hollow cylinder when the inside of the tract organ is in the other forms or shapes at a region around the lesion portion.

In a case where the endotract electrode 103a is to be applied to the esophagus, the bag-like member 112 may have about 6 to 25 mm of outer diameter and about 30 to 80 mm of length for example.

Figure 17:
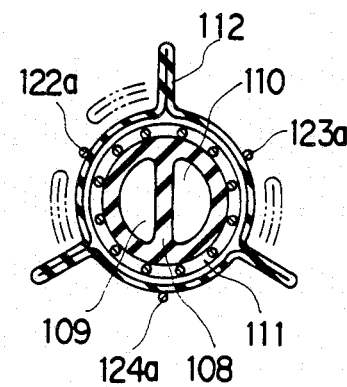

When the endotract electrode 103a is inserted into the tract organ, the bag-like member 112 of the electrode 103a is shriveled as shown by the solid lines of FIG. 17 and is preferably folded as shown by the imaginary lines of FIG. 17. The folded pattern of the bag-like member is not specified to a limited form, but it is desired to choose the pattern which ensures at least one of temperature detecting means described below to get into close contact with the lesion portion whose temperature is to be detected, when the bag-like member is unfolded.

The bag-like member may be made by forming a flexible tube or film of plastic material such as polyethylene or polypropylene into a desired shape, but is preferably made of a molded tube or balloon of silicone rubber in view of its least fear of toxicity to the living body.

In this specification "flexible bag-like member having sizes large enough to be contacted with an inner surface of the tract organ without being expanded" is meant to have characteristics for example that, when the bag-like member 112 is unfolded to a predetermined shape or form as shown in FIGS. 12 to 16 at the inside of the tract organ by the introduction of the cooling liquid into an inside 121 of the bag-like member 112 through an inlet aperture 120 communicated with the introducing passage 109 of the two-channel tube 108, the bag-like member 112 can be transformed from the folded state to the unfolded state even by a relatively low pressure of the cooling liquid at the inside 121 of the bag-like member (flexibility), and the membrane or film of the bag-like member 112 is not substantially stretched in the deformation or transformation from the folded state to the unfolded state thereof (relatively large size). In other words, the liquid pressure at the variable volume chamber 121 in the bag-like member 112 serves mainly to unfold the bag-like member 112 from the folded state thereof so that the bag-like member 112 can be made in close contact with the inner surface of the tract organ, while the liquid pressure at the chamber 121 is not intended to press the membrane of the bag-like member 112 onto the inner surface or wall of the tract organ. The pressure of the bag-like member 112 onto the inner wall of the tract organ is normally less that about 500 mmAq., and is desired no to exceed 1,000 mmAq.

The bag-like member 112 may have wrinkles at some portions thereof where the membrane of the member 112 is not completely unfolded when the bag-like member or element 112 has been made in the unfolded state thereof to be in close contact with the wall of the tract organ.

References 122a, 123a, 124a, 125a and 126a respectively represent hot or warm contact points or junctions of copperconstantan thermocouples 122, 123, 124, 125 and 126 serving as the temperature detecting means. The thermocouples 122, 123, 124, 125 and 126 are fixed by adhesives on the outer surface of the bag-like member 112 so that they can get into close contact with the inner surface of the tract organ when the bag-like member 112 is unfolded by the cooling liquid therein. Fixing of the thermocouples on the outer-surface of the bag-like member 112 are carried out by means of the adhesives of silicone resin, in which the balloon-like member 112 is kept expanded or unfolded during the fixing process.

Figure 12:
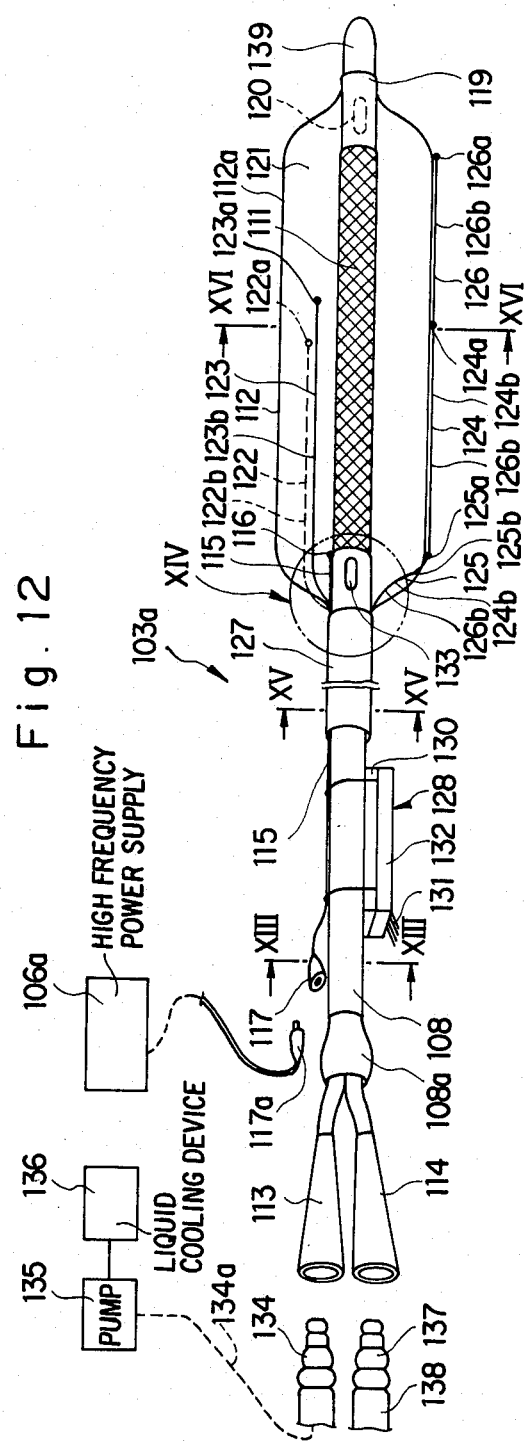
Figure 13:
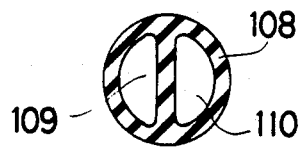
Figure 16:
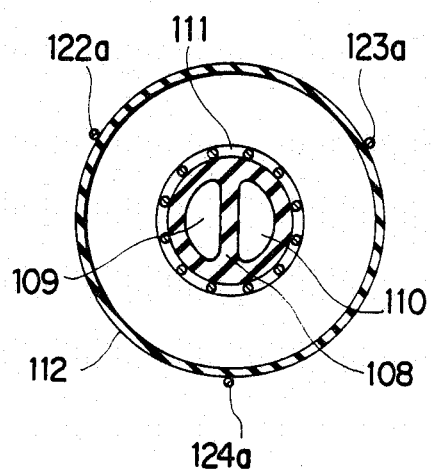

The contacts or junctions 122a, 123a and 124a are disposed at circumferentially equally spaced positions by 120° from each other in a central or intermediate portion of the bag-like member 112 in terms of its length as shown in FIGS. 12 and 16, and serve for observing the distribution of the temperature of the wall of the tract organ along the circumferential direction thereof at the axially central portion of the electrode element 111. The temperature observation along the circumferential direction may be carried out at more than or equal to four points or at two or one point(s).

The contacts 125a and 126a are disposed at the either side of the contact 124a. The contacts 125a, 124a and 126a serve for observing or supervising the distribution of the temperature of the wall or lesion portion of the tract organ along the longitudinal or axial direction of the tract organ. The temperature observation along the longitudinal direction may be carried out at more than or equal to four points or at two or one point(s).

The temperature detecting means may be chromel-alumel or other thermocouples instead of the copper-constantan thermocouples, or may be other temperature sensors such as thermistor instead of the thermocouples.

When the heat dissipation through the bag-like member 112 is not negligible, the output detected by the temperature detecting means does not strictly or accurately represent the temperature at the surface of the living body, but is useful for supervising, managing or evaluating the degree or level of the heating. Moreover, it should be noted that the desired operation of the bag-like member 112 is not prevented or affected in the electrode 103a even when the metallic lead wires 122b, 123b, 124b, 125b and 126b of the thermocouples 122, 123, 124, 125 and 126 are fixed by adhesives on and along the outer surface of the bag-like member 112, because the bag-like member 112 is not to be substantially stretched or expanded.

Figure 14:
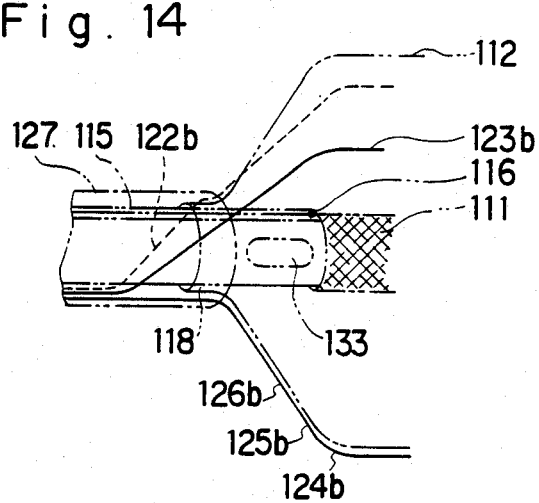
Figure 15:
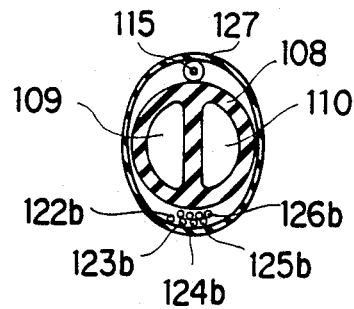

The lead wires 122b, 123b, 124b, 125b and 126b of the thermocouples 122, 123, 124, 125 and 126 are fixed on the outer circumference of the central portion of the tube 108 together with the lead wire 115 and the end portion 118 of the bag-like member 112 by the heat-shrinkable tube 127 made of silicone, where the lead wires 122b, 123b, 124b, 125b and 126b of the thermocouples 122 to 126 are not substantially crossed with the lead wire 115 for passing the high-frequency current therethrough. (The outer diameter of the tube 127 may be about 8 mm for example, in the case where the outer diameter of the tube 108 is about 6 mm and where the outer diameter of the lead wire 115 is about 1 mm.) More specifically, as shown in FIGS. 12, 14 and 15 for example, wires 115, 122b, 123b, 124b 125b and 126b are fixed by the tube 127 such that the lead wire 115 for the high-frequency current is extended along one side of the outer circumference of the tube 108, and that the lead wires 122b, 123b, 124b, 125b, and 126b for the temperature detection are extended along the other or opposite side of the outer circumference of the tube 8. Therefore there is little fear that the output or temperature signals transferred by the leads 122b, 123b, 124b, 125b and 126b may be affected to be varied due to the noises by the lead 115 or by the high-frequency current passing through the lead 115.

In addition, the tube 127 serves for improving the easy insertion and extraction of the endotract electrode 103a into and out of the tract organ.

The top end side 119 of the bag-like member is fixed to the tube 108 by means of the adhesive of the silicone group.

Figure 18:
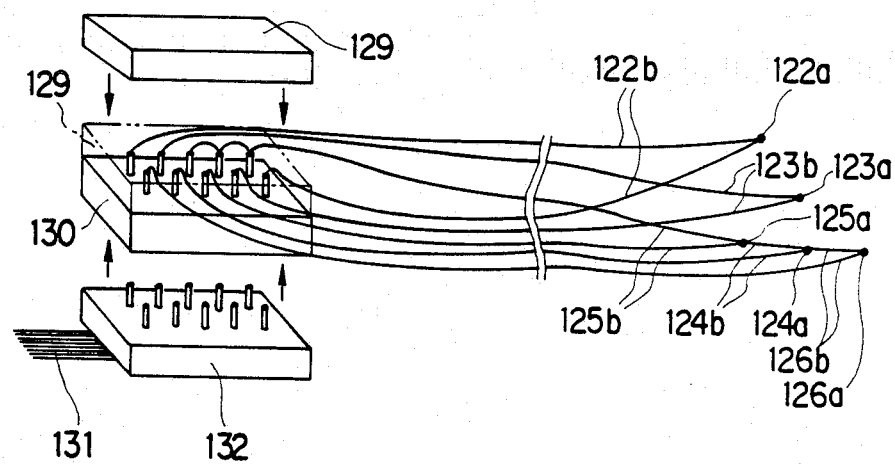

Reference numeral 128 represents a connector for the lead 122b, 123b, 124b, 125b and 126b of the thermocouples. The connector 128 comprises a 10-pins type of socket portion 130 to which leads 122b, 123b, 124b, 125b and 126b are electrically connected and fixed and to which a cap or cover part 129 is further fixed under pressure, and a 10-pins type of plug portion 132 detachably put in the socket portion 130, the plug portion 132 including lead wires connected to voltmeters (not shown) to indicate the temperatures at various portions of the tract organ as shown in FIGS. 12 and 18.

Reference numeral 133 denotes an outlet aperture communicated with the discharge passage 110 of the tube 108, and reference numeral 134 is a connector of the tube 134a for introducing the cooling liquid connected to a pump 135 and a liquid cooling device 136. The connector 134 is adapted to be detachably connected with the connector 113. A connector 137 is adapted to be detachably connected with the connector 114 so as to discharge or return the cooling liquid through a discharge tube 138.

In the meantime, the connectors 113 and 114 may be connected with the connectors 137 and 134 respectively such that the cooling liquid is introduced into the chamber 121 through the aperture 133 and is discharged from the chamber 121 through the aperture 120. Number of the apertures 120, 133 may be more than or equal to two respectively.

The operation of the device for hyperthermia having the first or endotract 103a thus constructed is explained hereinafter, while the details of the second or outer electrode will be explain later.

At first the endotract electrode 103a is inserted from a sealing cap 139 at the top end thereof into the tract organ to a predetermined depth while keeping the bag-like member 112 folded as shown by the imaginary lines of FIG. 17. After having inserted the electrode 103a into the tract organ so that the electrode element 111 thereof may be opposed to a lesion or tumor portion at the wall of the tract, the connectors 113, 114 are connected with the complementary connectors 134, 137, and the cooling liquid is started to be introduced into the inside 121 of the bag-like member 112 from the pump 135 through the introducing passage 109 and aperture 120 which have relatively low resistance to the flow.

It is preferable that the cooling liquid essentially consists of a liquid having high d.c. resistance or being insulating for the direct current such as ion-exchanged water for reducing the power consumption in the chamber 121, but generally conductive liquid such as city water may be used.

When the bag-like member 112 is unfolded from the folded state thereof by the introduction of the cooling water into the chamber 121, bag-like member 112 as well as the contact 122a, 123a, 124a, 125a and 126a of the thermocouples on the outer surface of the bag-like member is made in close contact with the inner wall of the tract organ without exerting much pressure on the wall of the tract organ. Then the temperatures at the inner surface of the tract organ detected by the thermocouples 122 to 126 can be transferred in the form of the voltage signals through the leads 131 to the voltmeters (not shown) to be indicated.

The cooling water introduced into the chamber 121 flows the chamber 121 generally axially, and then is discharged through the aperture 133, discharging passage 110 and the tube 138 whose resistances to the flow are relatively low or small.

On the other hand, high-frequency power supply 106a is switched on so as to start giving the high-frequency current between the electrode element 111 of the endotract electrode 103a and the opposed outer electrode such as the electrode 105 through the connectors 117, 117a, etc. The lesion portion at the wall of the tract organ near the endotract electrode 103a where the high electric field is produced can be heated or warmed at a desired temperature by manually or automatically adjusting the output power of the high-frequency power supply 106a, the temperature of the cooling water from the cooling device 136, and the flow rate of the coolingwater from the pump 135 for example. The circulated cooling water serves for preventing the inner surface of the tract organ in contact with the bag-like member 112 and the electrode element 111 from being overheated.

After the desired period of heating treatment, the power supply 106a is switched off, and the supply of the cooling water is stopped. Then, the bag-like member 112 is shrinked by the discharge of the cooling water from the tube 138, thereafter the endotract electrode 103a is extracted out of the tract organ, after releasing the connections between connectors if desired.

In applying the endotract electrode 103a it is important to fit the sizes of the bag-like member 112 to the sizes of the tract organ around the lesion portion to be subjected to heating treatment, therefore it may be desired to prepare a plurality of bag-like members having different outer diameters and different lengths. It should be noted that the bag-like member 112 of the endotract electrode 103a can be closely contacted with the inner surface of the tract organ at a longitudinally wide region thereof without fear of exerting excessive pressure on the wall or the tract organ.

As described above, in the endotract electrode of said another preferred embodiment, as the bag-like member surrounding the electrode element and being adapted to define a variablevolume chamber where the cooling liquid is circulated is made much flexible and is adapted to be contacted with the inner wall of the tract organ without being expanded or stretched by the pressure of the cooling liquid, the bag-like member can get in contact with the inner wall of the tract organ by being unfolded in the tract organ without exerting excessive pressure on the inner wall of the tract organ. This embodiment of the first or endotract electrode also serves for selective heating of the lesion at the deep inside of the living body or patient, without giving much pains to the patient by placing this endotract electrode in a tract organ having the lesion portion and disposing a second or outer electrode at a desired position on the surface of the patient.

Figure 19:
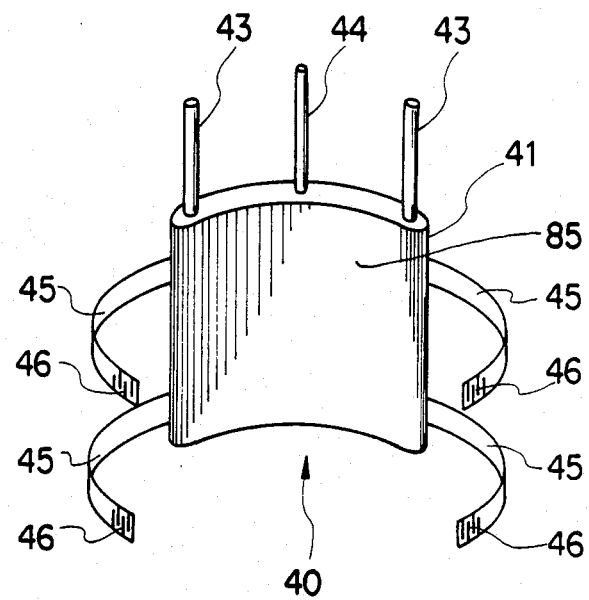
Figure 20:
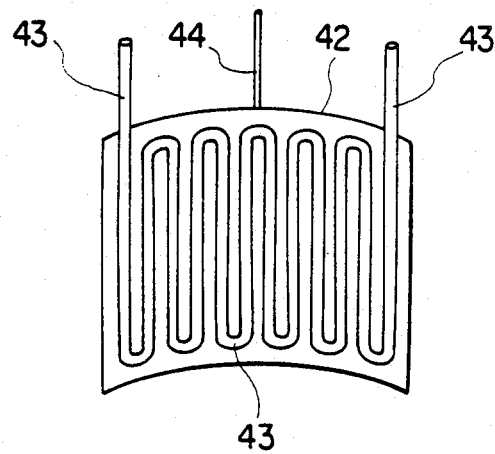

Reference will now be made to one example of a plate-like second electrode structure 40 adapted to be disposed on an outer circumference or surface of a living body to be heated by way of FIG. 19 and FIG. 20. FIG. 19 shows an outer look of the second electrode 40, in which an outer casing or bag-like member 41 is made of soft and flexible polymeric membrane such as plasticized polyvinylchloride so as to be easily closely contacted with the living body. As shown in FIG. 20, the outer casing 41 includes in its inside a flexible curved plate-like electrode element 42 made of a metal foil, braided metal wires or the like, of copper for example, and a water circulation tube 43 disposed on an inner or concave surface of the second electrode element 42. The electrode element 42 is connected through a lead wire 44 attached thereto to the terminal 81 of the high-frequency power supply 53 of FIG. 11 or a terminal of the high-frequency power supply 106a of FIG. 12 for example. The water circulation tube 43 is desirably made of soft and flexible material such as plasticized polyvinylchloride. The flow rate of the water circulated through the tube can be controlled by a pump means (not shown). The temperature of the water circulated through the tube 43 may be controlled by an appropriate cooling means if desired. The outer casing 41 is attached with soft and flexible bands 45, each having a pair of engaging parts 46, for fixing the second electrode main body 85 comprising the second electrode element 42, the tube 43 and the outer casing 41 to the outer circumference of a living body having a lesion portion to be heated. While it is desired to fill the inside of the outer casing 41 with an appropriate amount of water so that no air layer is formed between the electrode element 42 and the living body, other liquid or soft and flexible material having appropriate electrical factors (electric conductivity and dielectric constant) may be filled in place of water. Likewise, the liquid circulated through the circulation tube 43 is not necessarily restricted only to water. Since the electric field near the second electrode is rather weak and the amount of heat induced thereby is relatively small as described above, it is not always necessary to cool the part of the living body near the second electrode by means of the cooling liquid. In addition, bands 45 and engaging parts 46 may not be provided depending on the purposes of use. The area, or the length and width of the electrode element plate 42 can be determined by the position and the sizes of the lesion or part to be heated as well as by those of the first electrode and the area may, depending on the case, be large enough to cover the entire circumference of the living body. The shape of the electrode element 42 is not limited only to the rectangular shape but it may be any other shapes such as disc.

Upon applying the device for hyperthermia having the electrode pair as described above to the high-frequency heating treatment of a lesion at the tract organ of a living body, (1) the device can be inserted to and extracted from the inside of the tract organ with ease where the lesion or part to be heated is situated, (2) only the lesion portion at the deep inside of the living body near the first electrode that is a part to be heated can selectively be heated, and (3) the lesion at the deep inside of the living body can be heated selectively without causing undesirable heating and temperature rise in the surface layer, particularly, the subcutaneous fat layer as will be described more specifically in the following examples.

EXAMPLE 1

Figure 21:
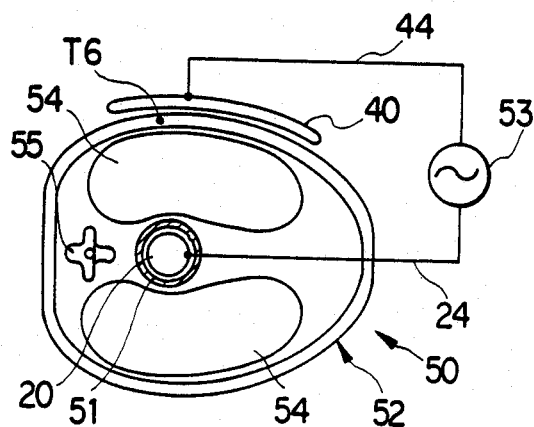
Figure 22:
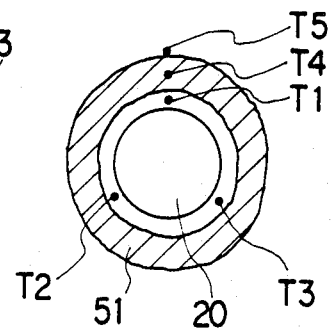
Figure 23:
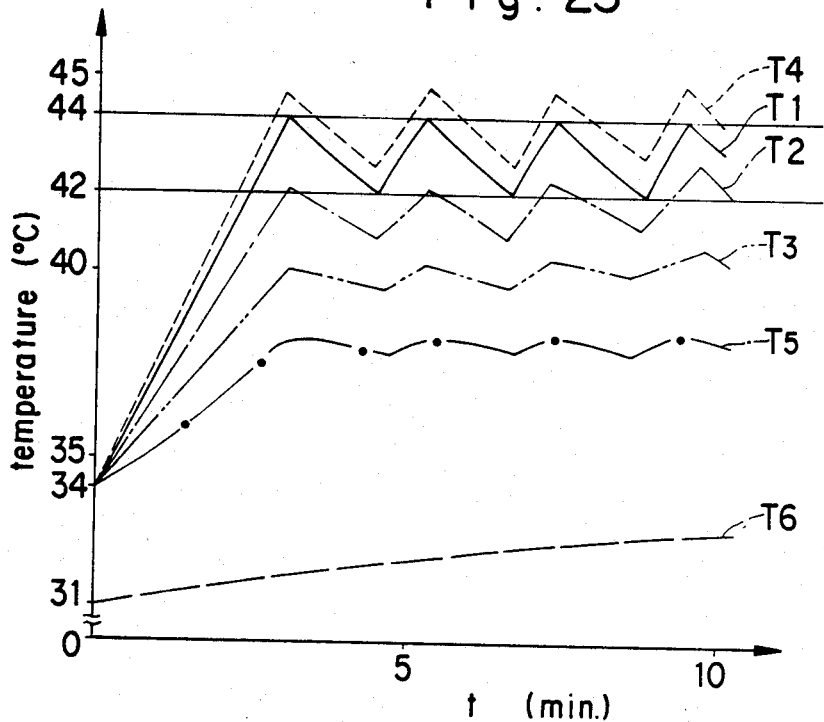

Description is to be made referring to FIGS. 21 through 23 about an example of an experiment on the heating of an esophagus 51 of a dog 50 as a living body wherein the first or endotract electrode 20 of FIG. 11 having the cylindrical first electrode element 21 was disposed to the inside of the esophagus 51, the plate-like second electrode structure 40 of FIG. 19 was disposed on the outer circumference at one side of a thorax part 52 of the dog 50, and the electrode elements 21, 42 of the two electrode structures 20, 40 were connected to the high-frequency power supply 53 (frequency: 13.56 MHz, power: 200 W).

FIG. 21 shows a cross section of the dog's thorax 52 and an arrangement of the electrodes 20, 40 employed for the experiment, in which are shown a cross section of the thorax part 52, esophagus 51, a lung 54 and a backbone 55. References T1 to T6 represent thin thermocouples coated with TEFLON TM (polytetrafluoroethylene) which are disposed at various positions for the measurement of temperature. As shown in FIG. 21, the thermocouple T6 was disposed in the subcutaneous fat layer on the side of the second electrode structure 40 and other thermocouples T1 to T5 were disposed near the esophagus 51. More specifically, as shown in FIG. 22 illustrating an enlarged view around the esophagus 51 the thermocouples T1 to T5 were disposed as follows; the thermocouple T1 was placed on the outer circumference of the endotract electrode 20 or of the bag-like member 30 at the side of the second electrode structure 40, the thermocouples T2 and T3 were placed at the two positions on the outer circumference of the bag-like member 30 of the endotract electrode 20 at the side remote from the second electrode structure 40, the thermocouple T4 was placed in the tissue of the esophagus 51 between the first and second electrodes 20, 40, and the thermocouple T5 was placed at the outer wall or outer surface of the esophagus 51 between the first and second electrodes 20, 40. In the experiment, the temperature signal detected by the thermocouple T1 was used for the ON-OFF control of the high-frequency power supply 53.

Specifically, the ON-OFF control was carried out cyclically by switching off the power supply 53 every time when the temperature detected by the thermocouple T1 reached an upper limit 44° C. and switching on the power supply 53 when the temperature detected by the thermocouple T1 decreased down to a lower limit 42° C.

FIG. 23 shows the relationship between the elapse of time t (min) and the change or variation in the temperature T (°C.) at each of the parts where the thermocouples were disposed. Before the start of the heating, the temperature designated or detected by the thermocouple T6 for the subcutaneous fat layer was 31° C. and the temperature designated or detected for other parts was 34° C. As the thermocouple T1 designated 44° C. about three minutes after the start of the heating, the power supply 53 was switched off and then the power supply 53 was switched on again for heating when the temperature decreased down to 42° C. after 1.5 min. (about 4.5 minutes after the start of the heating). And then after about one min. or less, the temperature increased up to 44° C. and the power supply 53 was switched off again. Such an ON-OFF control was repeated further. The temperature designated by the thermocouples T2 to T5 in or near the esophagus 51 changed in the similar manner as the temperature designated from the thermocouple T1. As compared with the temperature designated by the thermocouple T1, the temperature designated by the thermocouple T4 was higher by about 0.5° C., and each of the temperatures designated by the thermocouples T2, T3 and T5 was lower by about 1° C., about 2° C. and about 4° C. respectively. Although the temperature in the subcutaneous fat layer detected by the thermocouple T6 continued to increase slightly, the rising rate was only about 2° C. for 10 min, which shows substantially no danger of scalding. The increase in the temperature near the second electrode 40 can be suppressed further, if desired, by an appropriate means, for example by increasing the amount of the water circulated through the second electrode structure 40. The temperature designated by the thermocouple T4 situated remote from the endotract electrode 20 was somewhat higher than that by the thermocouple T1, because the portion near the thermocouple T1 was cooled by the water circulated through the first electrode 20.

As can be seen from the result of the above experiment, it has been confirmed that the esophagus 51 near the endotract electrode 20 can be heated selectively by the device for hyperthermia according to this invention.

The above-mentioned ON-OFF control may be made automatically by an appropriate control means connected to the power supply as well as to thermocouples. The thermocouples may be replaced by other temperature detecting means such as thermistors.

EXAMPLE 2

The first or endotract electrode 103a having the structure shown in FIGS. 12 to 17 were produced. In the electrode 103a, the electrode element 111 had 8 mm of outer diameter and 80 mm of length, the bag-like member 112 was made of silicone rubber, and had 15 mm of outer diameter at the enlarged diameter portion 112a when the membrane of the bag-like member 112 was not expanded or stretched under tensile force and 80 mm of length at the portion 112a, and the thickness of the membrane of the bag-like member 112 was 0.2 mm when the membrane was not expanded or stretched.

For the comparison, comparative endotract electrode having similar structure to that of the electrode 103a except that the bag-like member 112 of the electrode 103a was replaced with a bag-like member assembly having two bag-like members superposed in which an outer diameter of the enlarged diameter portion at the non-expanded state was 8 mm was prepared.

In the electrode 103a, the temperature detection was carried out by three thermocouples 122, 123, 124 whose contacts or junctions 122a, 123a, 124a were disposed at angular positions of 120° with each other on the outer surface of the bag-like member 112. On the other hand, in the comparative electrode, three thermocouples were disposed similarly at the angular positions of 120° with each other, but at positions between the two superposed bag-like members of the bag-like member assembly.

Each of the experiments on the endotract electrode 103a and on the above-mentioned comparative electrode was made as follows; the electrode 103a or the comparative electrode was inserted into a stomach of a dog, where the stomach had been processed in the form of a tube having an inner diameter of about 12 mm beforehand. The cooling liquid was circulated through the bag-like member 112 of the electrode 103a or through the bag-like member assembly of the comparative electrode to make the bag-like member 112 or the bag-like member assembly contacted with the inner surface of the stomach. On the other hand, an outer or second electrode plate was fixed on the belly of the dog, and the high-frequency current was intermittently supplied between the outer electrode and the endotract electrode 103a, or between the outer electrode and the comparative electrode by a high-frequency power supply (13.56 MHz, 100 W) to heat the wall of the stomach of the dog.

The internal pressure required to unfold the bag-like member 112 of the endotract electrode to a predetermined shape was approximately 500 mmAq., while the internal pressure required to expand or inflate the bag-like member assembly up to 12 mm in the outer diameter was as much as 3,000 mmAq.

Figure 24:
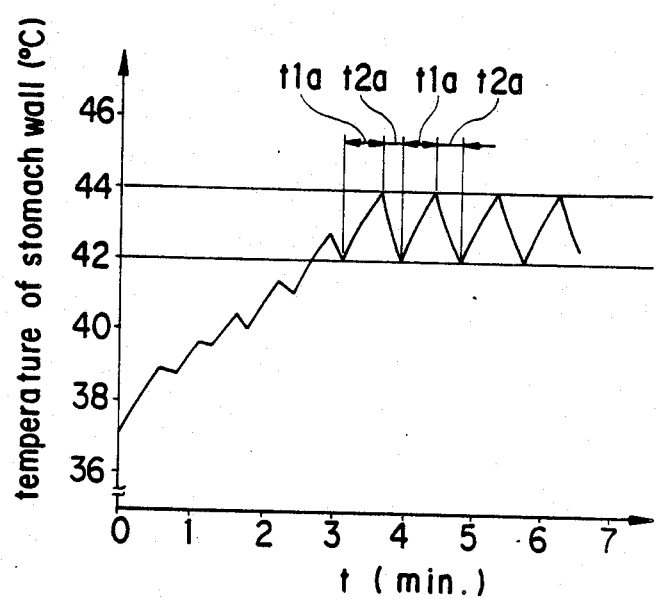
Figure 25:
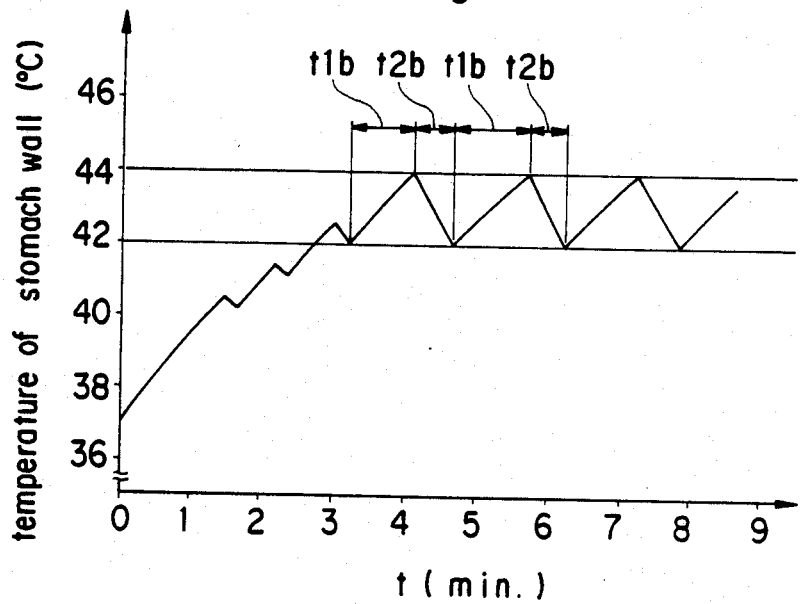

The heating and cooling pattern, similar to that of FIG. 23, obtained by the above-mentioned intermittent heating using the endotract electrode 103a is shown in FIG. 24, and the heating and cooling pattern obtained by the above-mentioned intermittent heating using the comparative electrode is shown in FIG. 25.

As is apparent from FIGS. 24 and 25, the period of time t1a required to warm the stomach wall by 2 degrees from 42° C. to 44° C. was about 30 seconds, and the period of time t2a required to be cooled from 44° C. to 42° C. was about 20 seconds in the case where the endotract electrode 103a was used (FIG. 24), while under the same conditions the period of time t1b required to be warm the stomach wall by 2 degrees from 42° C. to 44° C. was about 50 seconds, and the period of time t2b required to be cooled from 44° C. to 42° C. was about 30 seconds in the case where the comparative electrode was used.

This difference in the speed of response or speed of the change in the temperature of the stomach wall suggests that the resistance to heat flow at the contact between the wall of the stomach and the bag-like member 112 of the endotract electrode 103a is less than that between the stomach wall and the bag-like assembly of the comparative electrode because the bag-like member 112 of the endotract electrode 103a can be closely contacted with the inner surface of the stomach compared with the comparative electrode.

In each of the FIGS. 24 and 25, the axis of ordinates corresponds to a temperature detected by a thermocouple which indicated the highest temperature among the three thermocouples of the endotract electrode 103a or of the comparative electrode.

The difference between the highest temperature and the lowest temperature among the temperatures detected by the three thermocouples at each point of time was not more than 2 degrees in case of the electrode 103a, but it was as much as 3 degrees in case of the comparative electrode.

This results suggest that the endotract electrode 103a is more useful than the comparative electrode when the electrodes are used as the first or endotract electrode of the device for hyperthermia therapy which will be intended to heat the wall of the tumors at a temperature of 42° to 45° C. for 0.5 to several hours, because the electrode 103a can warm the lesion portion more uniformly than the comparative electrode.

As for the impedance matching with the living body, the endotract electrode 103a enabled a stable matching and to heat at a SWR (standing wave ratio) less than 1.5, on the other hand, in case of the comparative electrode, the SWR frequently increased, and therefore it was required to readjust or modify the matching condition. Furthermore it was difficult to maintain the SWR less than 2 in case of the comparative electrode.

What is claimed is:

1. A device for hyperthermia comprising:
   a radio frequency power supply having a pair of output terminals for delivering a radio-frequency of electric energy therefrom;
   first electrode means having a flexible electrode connected at one end thereof electrically with one of said pair of output terminals of said radio-frequency power supply through a conductive lead, said flexible elctrode being adapted to be disposed in a tract organ of a living body;
   second electrode means connected electrically with the other of said pair of output terminals of the radio-frequency power supply, wherein said second electrode means is adapted to be disposed on an outer circumference of the living body such that the second electrode means is opposed to said flexible electrode so as to generate a spatially inhomogeneous electric field with in the living body in cooperation with the flexible electrode such that part of the living body near the flexible electrode may be heated more strongly than a part of the living body near the second electrode means;
   a flexible bag-like member adapted to be fitted on an inner surface of the tract organ and surrounding the flexible electrode; and
   flexible tube means disposed at one end portion thereof inside the bag-like member, sealed at one leading end of said one end portion and provided with first aperture means on said one end portion for introducing a cooling liquid, said cooling liquid comprising at least in part water, into an inside of the flexible bag-like member and with second aperture means on said one end portion for discharging said cooling liquid out of the inside of the flexible bag-like member,
   the flexible bag-like member being fixed at both ends thereof to an outer circumference of the flexible tube means in the vicinity of positions where said first and second aperture means are provided,
   the flexible tube means being provided at said one end portion thereof with said flexible electrode.

2. The device according to claim 1, wherein said flexible electrode comprises:
   a tube-like member fitted around the outer circumference of said flexible tube means.

3. The device according to claim 2, wherein said tube-like member comprises:
   a braided metallic wire.

4. The device according to claim 2, wherein said tube-like member comprises:
   a conductive and flexible member.

5. The device according to claim 1, wherein said flexible electrode comprises:
   bellows fitted around the outer circumference of the flexible tube means.

6. The device according to claim 2, wherein said flexible electrode comprises:
   a helical element fitted around the outer circumference of the flexible tube means.

7. The device according to claim 2, wherein said flexible tube means passes through a space enclosed within said tube-like member.

8. The device according to claim 1, wherein the flexible bag-like member has a size large enough to be contacted with the inner surface of the tract organ without being substantially expanded.

9. The device according to claim 1 or 8, wherein said flexible bag-like member comprises:
   a polymeric material.

10. The device according to claim 1, wherein said flexible tube means further comprises:
    a guiding portion at the end thereof that is introduced into the tract organ for facilitating an introduction of the bag-like member into the tract organ.

11. The device according to claim 1 or 10, wherein the flexible tube means comprises:
    a two-channel tube in which a passage for introducing the cooling liquid and a passage for discharging the cooling liquid are integrally formed.

12. The device according to claim 1 or 10, wherein the flexible tube means comprises:
an outer tube,
an inner tube disposed in the inside portion of said outer tube;
an annular sealing plug disposed in a position corresponding to an intermediate position of said flexible electrode on the outer tube to thereby divide an annular space defined by an outer circumference of the inner tube and an inner circumference of the outer tube into a first annular space and a second annular space, and
with the first aperture means comprising
an opening at one end of the inner tube, the first annular space and a plurality of penetrating holes provided through the outer tube for communicating the first annular space with the inside of the flexible bag-like member, and the second aperture means comprising the second annular space and a plurality of penetrating holes provided through the outer tube for communicating the second annular space with the inside of the flexible bag-like member.

13. The device according to claim 1, wherein said device further comprises:
means for detecting temperature at an outer circumference of the flexible bag-like member.

14. The device according to claim 1, wherein the second electrode means is in the form of a hollow cylinder.

15. The device according to claim 1, wherein the second electrode means is in the form of a curved plate.

16. The device according to claim 1, wherein the second electrode means comprises:
an electrode element made of a flexible plate-like member, and a passage means for circulating cooling liquid, the passage means being disposed on a surface of the flexible plate-like member.

17. An endotract electrode for use in a device for radio-frequency hyperthermia, which is adapted to be disposed in a tract organ comprising:
a flexible electrode for producing a spatially inhomogenous radio-frequency electric field,
a flexible bag-like member adapted to be fitted on an inner surface of the tract organ and surrounding the flexible electrode, and
flexible tube means disposed at one end portion thereof inside the bag-like member, sealed at one leading end of said one end portion and provided with first aperture means on said one end portion for introducing a cooling liquid, said cooling liquid comprising at least in part water, into an inside of the flexible bag-like member and with second aperture means on said one end portion for discharging said cooling liquid out of the inside of the flexible bag-like member,
the flexible bag-like member being fixed at both ends thereof to an outer circumference of the flexible tube means in the vicinity of positions where said first and second aperture means are provided,
the flexible tube means being provided at said one end portion thereof with said flexible electrode.

18. The endotract electrode according to claim 17, wherein the flexible electrode comprises:
a tube-like member fitted around the outer circumference of the flexible tube means.

19. The endotract electrode according to claim 18, wherein said tube-like member comprises:
a braided metallic wire.

20. The endotract electrode according to claim 18, wherein said tube-like member comprises:
a conductive and
flexible member.

21. The endotract electrode according to claim 17, wherein said flexible electrode comprises:
bellows fitted around the outer circumference of the flexible tube means.

22. The endotract electrode according to claim 18, wherein said flexible electrode comprises a helical element fitted around the outer circumference of the flexible tube means.

23. The endotract electrode according to claim 18, wherein said flexible tube means passes through a space enclosed with said tube-like member.

24. The endotract electrode according to claim 17, wherein the flexible bag-like member has a size large enough to be contacted with the inner surface of the tract organ without being substantially expanded.

25. The endotract electrode according to claim 17 or 24, wherein the flexible bag-like member comprises a polymeric material.

26. The endotract electrode according to claim 17, wherein the flexible tube means further comprises:
a guiding portion at the end thereof that is introduced into the tract organ for facilitating an introduction of the bag-like member into the tract organ.

27. The endotract electrode according to claim 17, or 26, wherein the flexible tube means is a two-channel tube in which a passage for introducing the cooling liquid and a passage for discharging the cooling liquid are integrally formed.

28. The endotract electrode according to claim 17 or 26, wherein the flexible tube means comprises:
an outer tube, an inner tube disposed in an inside of said outer tube and an annular sealing plug disposed in a position corresponding to an intermediate position of the flexible electrode on the outer tube to thereby divide an annular space defined by an outer circumference of the inner tube and an inner circumference of the outer tube into a first annular space and a second annular space, the first aperture means comprises an opening at one end of the inner tube, the first annular space and a plurality of penetrating holes provided through the outer tube for communicating the first annular space with the inside of the flexible bag-like member, the second aperture means comprising the second annular space and a plurality of penetrating holes provided through the outer tube for communicating the second annular space with the inside of the flexible bag-like member.

29. The endotract electrode according to claim 17, wherein the endotract electrode further comprises:
means for detecting temperature at an outer circumference of the flexible bag-like member.

* * * * *